(12) United States Patent
Kang et al.

(10) Patent No.: US 11,419,562 B2
(45) Date of Patent: Aug. 23, 2022

(54) BIO-INFORMATION MEASURING APPARATUS AND BIO-INFORMATION MEASURING METHOD

(71) Applicant: SAMSUNG ELECTRONICS CO., LTD., Suwon-si (KR)

(72) Inventors: Jae Min Kang, Seoul (KR); Yong Joo Kwon, Yongin-si (KR); Sang Yun Park, Hwaseong-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 915 days.

(21) Appl. No.: 16/130,574

(22) Filed: Sep. 13, 2018

(65) Prior Publication Data

US 2019/0313979 A1 Oct. 17, 2019

(30) Foreign Application Priority Data

Apr. 12, 2018 (KR) .................. 10-2018-0042837

(51) Int. Cl.
| | |
|---|---|
| *A61B 5/00* | (2006.01) |
| *A61B 5/02* | (2006.01) |
| *A61B 5/021* | (2006.01) |
| *A61B 5/024* | (2006.01) |
| *A61B 5/16* | (2006.01) |
| *A61B 90/00* | (2016.01) |

(52) U.S. Cl.
CPC ........ *A61B 5/7278* (2013.01); *A61B 5/02007* (2013.01); *A61B 5/02116* (2013.01); *A61B 5/02427* (2013.01); *A61B 5/165* (2013.01); *A61B 5/6843* (2013.01); *A61B 2090/064* (2016.02); *A61B 2562/0247* (2013.01); *A61B 2562/0261* (2013.01)

(58) Field of Classification Search
None
See application file for complete search history.

(56) References Cited

U.S. PATENT DOCUMENTS

| | | |
|---|---|---|
| 2008/0228089 A1 | 9/2008 | Cho et al. |
| 2012/0203080 A1 | 8/2012 | Kim et al. |
| 2016/0198955 A1 | 7/2016 | Fortin |
| 2016/0220128 A1* | 8/2016 | Den Brinker ........ A61B 5/0008 |

(Continued)

FOREIGN PATENT DOCUMENTS

| | | |
|---|---|---|
| JP | 2006-239114 A | 9/2006 |
| JP | 2008-212258 A | 9/2008 |

(Continued)

OTHER PUBLICATIONS

Communication dated May 13, 2019, issued by the European Patent Office in counterpart European Application No. 19165370.8.

*Primary Examiner* — Yi-Shan Yang
(74) *Attorney, Agent, or Firm* — Sughrue Mion, PLLC

(57) ABSTRACT

A bio-information measuring apparatus includes: a pulse wave measurer configured to measure a plurality of pulse wave signals from an object; a contact pressure measurer configured to measure contact a pressure between the object and the pulse wave measurer; and a processor configured to obtain a plurality of first envelopes based on the contact pressure and the plurality of pulse wave signals, obtain a second envelope by combining the plurality of first envelopes, and measure bio-information based on the second envelope.

24 Claims, 20 Drawing Sheets

(56) References Cited

U.S. PATENT DOCUMENTS

| | | | |
|---|---|---|---|
| 2017/0095168 A1 | 4/2017 | Kwon et al. | |
| 2017/0215749 A1* | 8/2017 | Zhuo | A61B 5/02055 |
| 2017/0319146 A1 | 11/2017 | Park et al. | |
| 2017/0367597 A1 | 12/2017 | Fortin | |
| 2018/0085011 A1* | 3/2018 | Ma | A61B 5/7235 |
| 2021/0298618 A1* | 9/2021 | Mukkamala | A61B 5/6898 |

FOREIGN PATENT DOCUMENTS

| | | |
|---|---|---|
| JP | 4726085 B2 | 7/2011 |
| JP | 2016-152918 A | 8/2016 |
| WO | 2016/110781 A1 | 7/2016 |
| WO | 2017/152098 A1 | 9/2017 |

\* cited by examiner

TIME (Sample Frequency 270Hz)

BIO-INFORMATION MEASURING APPARATUS AND BIO-INFORMATION MEASURING METHOD

CROSS-REFERENCE TO RELATED APPLICATION(S)

This application claims priority from Korean Patent Application No. 10-2018-0042837, filed on Apr. 12, 2018 in the Korean Intellectual Property Office, the disclosure of which is incorporated herein by reference in its entirety.

BACKGROUND

1. Field

Apparatuses and methods consistent with exemplary embodiments relate to bio-information measurement, and more particularly to cuffless blood pressure measurement.

2. Description of the Related Art

As a method of measuring blood pressure in a non-invasive manner without damaging a human body, there is a method of measuring blood pressure by using cuff pressure measurements and a method of measuring blood pressure by using pulse wave measurements without using a cuff.

As a method of measuring blood pressure using cuff measurements, there is a Korotkoff-sound method which measures blood pressure by winding a cuff around an upper arm and hearing the audible sound of blood vessels through a stethoscope while decreasing pressure in the cuff after increasing it; and an Oscillometric method, which is employed by an automated device, and measures blood pressure by winding a cuff around an upper arm, continuously measuring pressure in the cuff while gradually decreasing cuff pressure after increasing it, and measuring blood pressure based on a point where a pressure signal is changed substantially.

As a method of cufflessly measuring blood pressure, there is a method of estimating blood pressure by calculating a Pulse Transit Time (PTT), and a Pulse Wave Analysis (PWA) method of estimating blood pressure by analyzing a pulse wave form.

SUMMARY

According to an aspect of an exemplary embodiment, there is provided a bio-information measuring apparatus, including: a pulse wave measurer configured to measure a plurality of pulse wave signals from an object; a contact pressure measurer configured to measure contact pressure between the object and the pulse wave measurer; and a processor configured to obtain a plurality of first envelopes based on the contact pressure and the plurality of pulse wave signals, obtain a second envelope by combining the plurality of first envelopes, and measure bio-information based on the obtained second envelope.

The pulse wave measurer may include: a plurality of light emitters configured to emit a light onto the object; and one or more light receivers configured to receive the light reflected from the object.

The plurality of light emitters may be disposed at different distances from the one or more light receivers.

The plurality of light emitters may emit the light of different wavelengths.

The contact pressure measurer may include at least one of an area sensor, a force sensor, a pressure sensor, and a strain gauge.

The processor may include an envelope combiner configured to obtain the second envelope by applying the plurality of first envelopes in a linear function equation.

The envelope combiner may obtain the one second envelope by selecting two or more first envelopes from among the plurality of first envelopes according to predetermined criteria, and by applying the selected two or more first envelopes in the linear function equation.

The envelope combiner may calculate a coefficient of the linear function equation for each of the plurality of first envelopes.

The envelope combiner may calculate a reciprocal number of a maximum amplitude value of each of the plurality of first envelopes as the coefficient for each of the plurality of first envelopes.

In addition, the processor may further include: a feature extractor configured to extract features from the second envelope; and a measurer configured to measure bio-information based on the extracted features.

In this case, the features may include one or more of a contact pressure value and an amplitude value at a maximum peak point of the second envelope, and a contact pressure value and an amplitude value at certain points in a predetermined range based on the maximum peak point.

The bio-information may include at least one of blood pressure, vascular age, degree of arteriosclerosis, aortic pressure waveform, vascular compliance, stress index, and degree of fatigue.

Further, the bio-information measuring apparatus may further include an output interface configured to output, upon receiving a request for measuring the bio-information, guide information comprising at least one of a position of the object that is in contact with the pulse wave measurer, a reference contact pressure value obtained during measurement of a reference pulse wave signal, and a contact pressure value measured during measurement of the plurality of pulse wave signals of the object.

Once bio-information is measured, the output interface may further output a measurement result of the bio-information.

According to an aspect of an exemplary embodiment, there is provided a bio-information measuring method including: measuring a plurality of pulse wave signals from an object; measuring contact pressure between the object and the pulse wave measurer, obtaining a plurality of first envelopes based on the contact pressure and the plurality of pulse wave signals; obtaining a second envelope by combining the plurality of first envelopes; and measuring bio-information based on the obtained second envelope.

In this case, the plurality of pulse wave signals may be multi-wavelength pulse wave signals measured at a plurality of positions on the object.

The obtaining of the second envelope may include obtaining the second envelope by applying the plurality of first envelopes in a linear function equation.

The obtaining of the second envelope may include obtaining the one second envelope by: selecting two or more first envelopes from among the plurality of first envelopes according to predetermined criteria; and applying the selected two or more first envelopes in the linear function equation.

The obtaining of the second envelope may include calculating a coefficient of the linear function equation for each of the plurality of first envelopes.

The measuring of bio-information may include: extracting features from the second envelope; and measuring bio-information based on the extracted features.

In addition, the bio-information measuring method may further include, upon receiving a request for measuring the bio-information, outputting guide information that prompts a user to gradually increase the contact pressure exerted onto the pulse wave measurer.

Further, the bio-information measuring method may further include, once bio-information is measured, outputting a measurement result of the bio-information.

The measuring the plurality of pulse wave signals may include measuring the plurality of pulse wave signals while the guide information is displayed and the contact pressure between the object and the pulse wave measurer gradually increases.

According to an aspect of an exemplary embodiment, there is provided a bio-information measuring apparatus, including: a pulse wave measurer configured to measure a plurality of pulse wave signals from an object; a contact pressure measurer configured to measure a contact pressure between the object and the pulse wave measurer; and a processor configured to obtain a plurality of envelopes based on the contact pressure and the plurality of pulse wave signals, obtain a second feature by combining a plurality of first features extracted from the plurality of envelopes, and measure bio-information based on the second feature.

The pulse wave measurer may include: a plurality of light emitters including one or more light sources to emit light onto the object; and a light receiver configured to receive the light reflected from the object.

The plurality of light emitters may be disposed at different distances from the light receiver, and may emit light of different wavelengths.

The processor may include: a feature extractor configured to extract the plurality of first features, including a contact pressure value at a maximum peak point, from each of the plurality of envelopes; and a feature combiner configured to obtain the second feature, including mean arterial pressure (MAP), by applying the plurality of first features in a linear function equation.

The processor may further include a measurer configured to measure a diastolic blood pressure (DBP) and a systolic blood pressure (SBP) based on the MAP.

According to an aspect of an exemplary embodiment, there is provided a bio-information measuring apparatus, including: a pulse wave measurer configured to measure a plurality of pulse wave signals from an object; a contact pressure measurer configured to measure contact pressure between the object and the pulse wave measurer; a processor configured to obtain a second envelope by combining a plurality of first envelopes obtained based on the contact pressure and the plurality of pulse wave signals, and to measure bio-information based on the obtained second envelope; and a communication interface configured to transmit a processing result of the processor to an external device, or to receive reference information from the external device.

The reference information may include one or more of a linear function equation for combining the plurality of first envelopes into one second envelope, information for calibrating the linear function equation, and measurement guide information.

Further, the bio-information measuring apparatus may further include a storage configured to store one or more of the processing result of the processor and the reference information.

The processor may determine whether to calibrate the linear function equation based on one or more of a measurement history of bio-information, a health state of a user, a position of an object, a state of an object, intensity of a light source, and information for calibration.

According to an aspect of an exemplary embodiment, there is provided a bio-information measuring apparatus, including: a contract pressure sensor configured to measure a contact pressure between a user and a pulse wave measurer; a pulse wave measurer comprising a light emitter and a light receiver to measure a plurality of pulse wave signals from the user while the contact pressure is gradually increasing or decreasing; and a processor configured to identify a plurality of envelopes of the plurality of pulse wave signals in a contact pressure domain, and obtain bio-information based on a combination of the plurality of envelopes, wherein the plurality of envelopes represent changes of amplitudes of the plurality of pulse wave signals while the contact pressure gradually increases or decreases.

The processor may be further configured to apply a plurality of weights to the plurality of envelopes, respectively, to obtain a weighted plurality of envelopes, and add up the weighted plurality of envelopes to obtain the combination of the plurality of envelopes.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
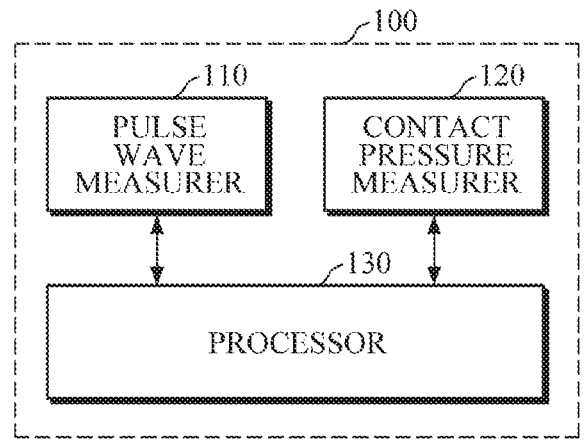
FIG. 1 is a block diagram illustrating a bio-information measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "including" will be understood to imply the inclusion of stated elements but not the exclusion of any other elements. Also, the terms, such as 'part' or 'module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating a bio-information measuring apparatus according to an exemplary embodiment.

Referring to FIG. 1, the bio-information measuring apparatus 100 includes a pulse wave measurer 110, a contact pressure measurer 120, and a processor 130.

The pulse wave measurer 110 may measure a photoplethysmography (PPG) signal (hereinafter referred to as a "pulse wave signal") from an object. In this case, the object may be a top portion of a wrist or a portion of veins or capillaries of a finger. However, the object is not limited thereto, and may be a bottom portion of the wrist where a radial artery passes.

The pulse wave measurer 110 may include a light emitter to emit light onto an object, and a light receiver to obtain a pulse wave signal by detecting the light which is emitted by the light emitter and is scattered or reflected from the object.

The light emitter includes one or more light sources to emit light onto an object, and may be a light emitting diode (LED), a laser diode (LD), or a fluorescent body. However, the light emitter is not limited thereto, and in the case where the light emitter includes a plurality of light sources, each of the light sources may emit light of different wavelengths. Further, the pulse wave measurer 110 may include a plurality of light emitters, and each of the light emitters may be disposed at different distances from the light receiver. In addition, each of the light emitters may emit light of different wavelengths.

The light receiver may be one or more in number, and may be, for example, a photo diode, a photo transistor (PTr), or an image sensor (e.g., CMOS image sensor). In the case where the pulse wave measurer 110 includes a plurality of light receivers, pulse wave signals obtained by each of the light receivers may be combined for each light emitter and each light source.

The contact pressure measurer 120 may measure contact pressure between the pulse wave measurer 110 and an object while the pulse wave measurer 110 measures pulse waves from the object. The contact pressure measurer 120 may include an area sensor, a force sensor, a pressure sensor using an airbag, a force matrix sensor which may measure a force for each pixel, or the like, but the contact pressure measurer 120 is not limited thereto.

The processor 130 may receive a request for measuring bio-information from a user or a connected external device. Upon receiving the request for measuring bio-information, the processor 130 may generate a control signal, and may control the pulse wave measurer 110 and the contact pressure measurer 120. The processor 130 may be electrically connected to the pulse wave measurer 110 and the contact pressure measurer 120.

The processor 130 may receive pulse wave signals and contact pressure signals from the pulse wave measurer 110 and the contact pressure measurer 120, respectively, and may measure bio-information based on the received pulse wave signals and contact pressure signals. In this case, bio-information may include mean arterial pressure (MAP), systolic blood pressure (SBP), diastolic blood pressure (DBP), vascular age, degree of arteriosclerosis, aortic pressure waveform, vascular compliance, stress index, and degree of fatigue, but is not limited thereto. For example, upon receiving a plurality of multi-wavelength pulse wave signals which are measured in a wide region of an object, the processor 130 may obtain a plurality of envelopes based on the received pulse wave signals and contact pressure signals, and may measure bio-information by using the plurality of envelopes.

Hereinafter, various exemplary embodiments of the processor 130 will be described with reference to FIGS. 2 and 3. The processor 130 is not limited to the exemplary embodiments and various modifications may be applied thereto.

Figure 2:
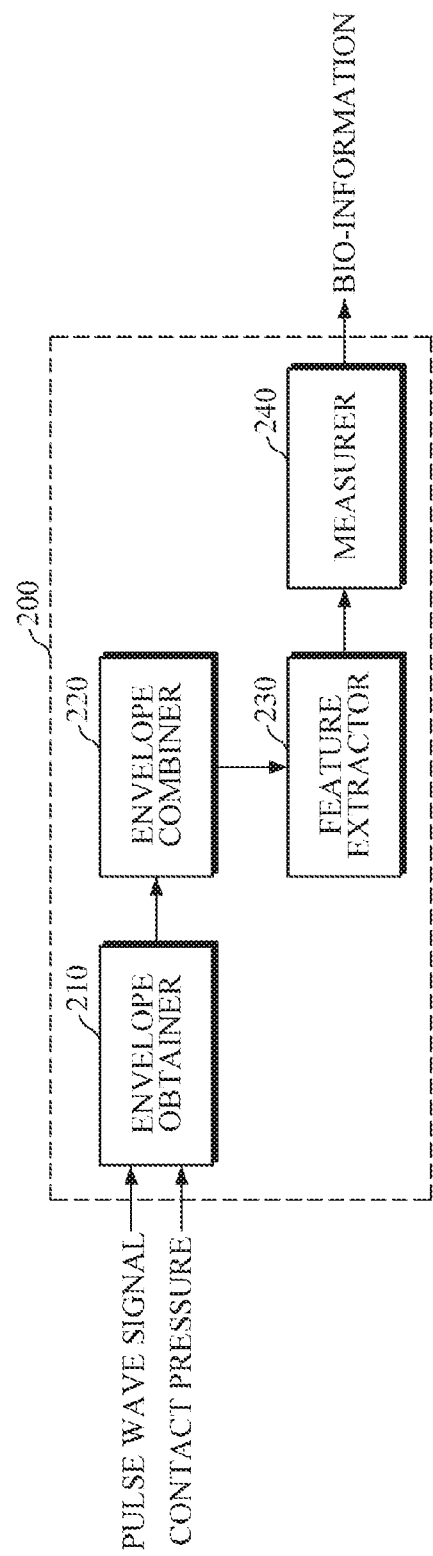
FIG. 2 is a block diagram illustrating a processor of FIG. 1 according to an exemplary embodiment.

FIG. 2 is a block diagram illustrating a processor 130 of FIG. 1 according to an exemplary embodiment.

Referring to FIG. 2, the processor 200 includes an envelope obtainer 210, an envelope combiner 220, a feature extractor 230, and a measurer 240.

The envelope obtainer 210 may obtain envelopes based on the pulse wave signals and the contact pressure signals, which are measured by the pulse wave measurer 110 and the contact pressure measurer 120 respectively for a predetermined period of time. Upon receiving the pulse wave signals from the pulse wave measurer 110, the envelope obtainer 210 may obtain first envelopes for each of the plurality of pulse wave signals based on the contact pressure signals.

For example, the envelope obtainer 210 may perform quadratic differential on each of the pulse wave signals, and may obtain a first envelope from each of the pulse wave signals by using a quadratic differential signal. For example, by plotting a peak-to-peak amplitude value of each quadratic differential signal based on contact pressure at the same measurement time as the peak-to-peak amplitude value, the envelope obtainer 210 may obtain the first envelope which represents an oscillometric waveform of a contact pressure versus pulse wave signal. In particular, the peak-to-peak value may be extracted by subtracting a negative amplitude value from a positive amplitude value of a waveform at each measurement time in a quadratic differential signal.

The envelope obtainer 210 may normalize each of the first envelopes. For example, the envelope obtainer 210 may normalize each of the first envelopes to be between 0 to 1 based on an amplitude value at a maximum peak point of each of the first envelopes.

Once the envelope obtainer 210 obtains the first envelopes for each of the plurality of pulse wave signals, the envelope combiner 220 may obtain a single envelope by combining the plural first envelopes. The single envelope obtained by combining the plural first envelopes may be referred to as a second envelope.

The processor 200 may apply a plurality of weights (e.g., coefficients $c_1$, $c_2$, and $c_3$) respectively to the first envelopes, to obtain a weighted plurality of envelopes (e.g., $c_1f_1$, $c_2f_2$, and $c_3f_3$) and add up the weighted plurality of envelopes to obtain the combination of the plurality of envelopes (e.g., $c_1f_1$, $+c_2f_2+c_3f_3$). For example, the envelope combiner 220 may obtain the second envelope by applying each of the first envelopes in a linear function equation as represented by the following Equation 1.

$$f_{total} = c_1f_1 + c_2f_2 + c_3f_3 \quad \text{[Equation 1]}$$

Herein, $f_1$, $f_2$, and $f_3$ denote the first envelopes respectively, $c_1$, $c_2$, and $c_3$ denote coefficients of the envelopes, and $f_{total}$ denotes the combined second envelope.

The coefficients $c_1$, $c_2$, and $c_3$ of each of the first envelopes may be pre-calculated by, for example, a bio-information measuring apparatus 100 or an external device, and may be applied thereto. For example, each of the coefficients may be pre-calculated through preprocessing based on types of device to which the coefficient is to be applied, an examination position, a size of a device, a light intensity of each light emitter, and/or a wavelength range, a health state of a user, but the coefficient is not limited thereto.

In another example, the envelope combiner 220 may dynamically calculate a coefficient of each first envelope. Once the first envelope is obtained for each pulse wave signal, the envelope combiner 220 may extract features for calculating a coefficient from each first envelope, and may calculate a coefficient by using the extracted features. In particular, the features for calculating the coefficient may include an amplitude value at a maximum peak point of each of the first envelopes, and each coefficient may be defined as a reciprocal number of an extracted amplitude value as shown in the following Equation 2. However, the coefficient is not limited thereto, and features and a mathematical equation for calculating the coefficient may be defined differently in consideration of the various requirements described above.

$$c_i = \frac{1}{\max(f_i)} \quad \text{[Equation 2]}$$

Herein, $c_i$ denotes the coefficient of an i-th first envelope $f_i$, max $(f_i)$ denotes an amplitude value at a maximum peak point of the i-th first envelope $f_i$ (i.e., a maximum amplitude value), and i denotes an integer of 1 or more.

The envelope combiner 220 may select some of the first envelopes, from among the plurality of first envelopes obtained by the envelope obtainer 210, according to predetermined criteria, and may obtain a second envelope by combining the selected first envelopes. In particular, the predetermined criteria may include amplitude values at peak points of the plurality of first envelopes, a distance between a light source and a light receiver for each of the plurality of first envelopes, and information on whether a maximum peak amplitude value is within a predetermined range of contact pressure values, but the criteria are not limited thereto, and may include various other criteria.

Once the envelope combiner 220 obtains the combined one second envelope, the feature extractor 230 may extract features for measuring bio-information from the obtained second envelope. In this case, the features for measuring bio-information may include a contact pressure value and an amplitude value at a maximum peak point, and a contact pressure value or an amplitude value at a certain point in a predetermined range (e.g., at points to the left or right of the maximum peak point in a ratio range of 0.5 to 0.7) based on the maximum peak point. However, the features for measuring bio-information is not limited thereto.

The measurer 240 may measure bio-information (e.g., blood pressure) based on the features extracted by the feature extractor 230. In the case in which contact pressure is changed during measurement of a pulse wave signal, an amplitude value of a pulse wave signal obtained from a body surface shows an increasing or a decreasing pattern, and the measurer 240 may measure bio-information, such as blood pressure, based on values of the increasing or the decreasing pattern.

For example, the measurer 240 may calculate, as the MAP, a contact pressure value which is extracted at a maximum peak point of the second envelope. Further, the measurer 240 may calculate, as the DBP and the SBP, contact pressure values which are at points to the left and right of the maximum peak point and have 0.5 to 0.7 of the value at the maximum peak point.

In another example, the measurer 240 may measure bio-information by using a pre-defined measurement model as represented by the following Equation 3.

$$y = ax + b \quad \text{[Equation 3]}$$

Herein, y denotes bio-information to be obtained, such as the DBP, the SBP, and/or the MAP, and x denotes the extracted feature value. Further, a and b denote values pre-calculated through preprocessing, and may be defined differently according to the types of bio-information (e.g., the DBP, the SBP, and/or the MAP). However, the bio-information is not limited thereto, and may be pre-generated in the form of a table in which feature values are mapped to blood pressure values.

Figure 3:
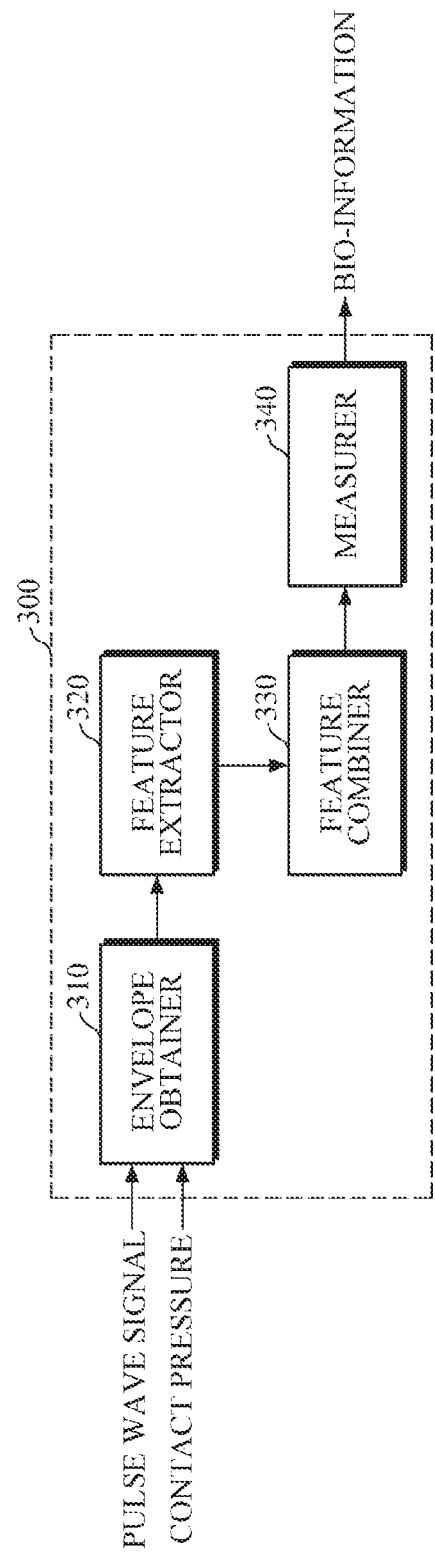
FIG. 3 is a block diagram illustrating the processor of FIG. 1 according to another exemplary embodiment.

FIG. 3 is a block diagram illustrating the processor 130 of FIG. 1 according to another exemplary embodiment.

Referring to FIG. 3, the processor 300 includes an envelope obtainer 310, a feature extractor 320, a feature combiner 330, and a measurer 340.

The envelope obtainer 310 may obtain envelopes for each pulse wave signal based on a plurality of pulse wave signals and contact pressure signals which are measured for a predetermined period of time. As described above, the plurality of pulse wave signals may be signals measured in a wide region of an object, and may be multi-wavelength pulse wave signals. For example, the envelope obtainer 310 may obtain the envelope, which is a waveform of contact pressure versus pulse wave amplitude, by plotting with an X axis as contact pressure values and a Y axis as pulse wave amplitude values at each measurement time.

Once the envelopes are obtained (e.g., for each of the pulse wave signals), the feature extractor 320 may extract a first feature from each of the obtained envelopes. For example, the first feature may include a contact pressure value and an amplitude value at a maximum peak point of each envelope, and a contact pressure value or an amplitude value at a certain point in a predetermined range based on the maximum peak point. However, the first feature is not specifically limited thereto.

The feature combiner 330 may obtain a single second feature by combining a plurality of first features extracted by the feature extractor 320. For example, the feature combiner 330 may obtain the single second feature by applying the first feature in a linear function equation as represented by the following Equation 4.

$$P_{total} = \alpha_1 P_1 + \alpha_2 P_2 + \alpha_3 P_3 \quad \text{[Equation 4]}$$

Herein. $P_1$, $P_2$, and $P_3$ denote the first features respectively, but the number thereof is not specifically limited thereto. $P_{total}$ denotes the combined second feature, and $\alpha_1$, $\alpha_2$, $\alpha_3$ are pre-defined constants.

The feature combiner 330 may select some of the first features from among the plurality of first features according to pre-defined criteria, and may obtain the one second feature by combining the selected first features.

Once a plurality of first features are extracted, the feature combiner 330 may dynamically calculate a coefficient of the above linear function Equation 4. For example, the first features extracted by the feature extractor 320 may include a maximum amplitude value at a maximum peak point of each envelope as described above, and the feature combiner 330 may calculate a reciprocal number of the maximum amplitude value as each coefficient, but the coefficient is not limited thereto. The coefficient may be a value pre-calculated by an external device through preprocessing and preset in the device, and may be updated periodically.

The measurer 340 may measure bio-information by using the obtained single second feature. For example, once the feature extractor 320 extracts each contact pressure value at a maximum peak point of each envelope as the MAP which is the first feature, and the feature combiner 330 obtains the combined MAP, which is the second feature, by combining each MAP, the measurer 340 may measure the MAP, the SBP, and the DBP based on the combined MAP as described above with reference to FIG. 2.

Figure 4:
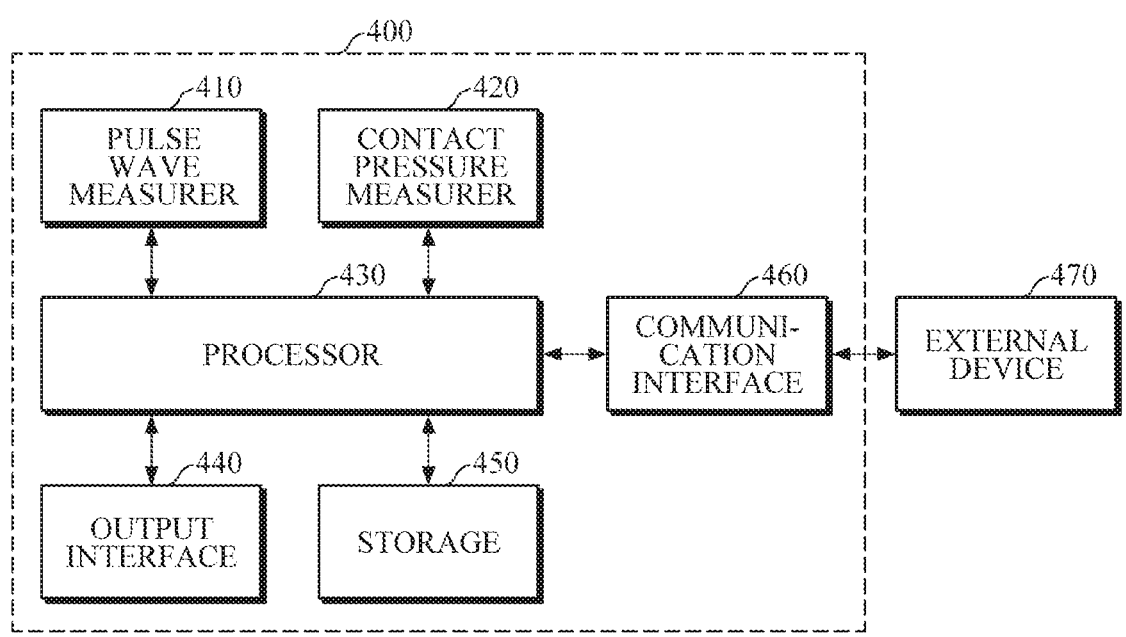
FIG. 4 is a block diagram illustrating a bio-information measuring apparatus according to another exemplary embodiment.

FIG. 4 is a block diagram illustrating a bio-information measuring apparatus according to another exemplary embodiment.

Referring to FIG. 4, the bio-information measuring apparatus 400 includes a pulse wave measurer 410, a contact pressure measurer 420, a processor 430, an output interface 440, a storage 450, and a communication interface 460. In the exemplary embodiment, the bio-information measuring apparatus 400 is configured based on the embodiments of the bio-information measuring apparatus 100 described above with reference to FIGS. 1 to 3, such that the following description will be made based on details that do not overlap.

The processor 430 may control various components of the bio-information measuring apparatus 400. For example, upon receiving bio-information, the processor 430 may generate a control signal to control the pulse wave measurer 410 and the contact pressure measurer 420.

Further, once bio-information is measured, the processor 430 may control the output interface 440 to output various types of information including a measurement result of bio-information. Once bio-information is measured, the processor 430 may analyze a health state of a user based on the measurement result, may generate alarm/warning information on a user's health based on the analysis, and may control the output interface 440 to output the generated information.

In addition, upon receiving bio-information, the processor 430 may control the output interface 440 to guide a user to increase or decrease contact pressure during a measurement time period. Moreover, the processor 430 may control the communication interface 460 to transmit and receive various types of information with an external device 470.

The processor 430 may determine whether to calibrate a linear function equation based on a measurement history of bio-information, a health state of a user, a position of an object, a state of an object, intensity of a light source, and/or information for calibration. For example, the processor 430 may periodically determine whether to calibrate a linear function equation. Alternatively, once bio-information is measured, the processor 430 may determine whether there is abnormality in a current measurement result based on a previous bio-information measurement history; and upon determining that there is abnormality, the processor 430 may determine to calibrate a linear function equation. In addition, in the case in which a health state of a user is changed or a position of an object is changed, the processor 430 may determine to re-calibrate a linear function equation. However, determination on calibration is not limited thereto.

Upon determining to calibrate a linear function equation, the processor 430 may calibrate the linear function equation by receiving, from an external device 470, reference information to be used for the calibration. Alternatively, the processor 430 may update a pre-stored linear function equation by receiving the calibrated linear function equation directly from the external device 470.

The output interface 440 may visually output a measurement result of bio-information and alarm/warning information or may output the information non-visually in voice or through a haptic sense under the control of the processor 430. For example, in the case in which a measured blood pressure value falls outside a user's normal blood pressure range, the output interface 440 may display the blood pressure value in red, or may provide a warning through vibration using a haptic module. Alternatively, the output interface 440 may notify a user of the occurrence of abnormality in voice, and may provide guide information on an action to be taken by the user.

Further, the output interface 440 may output guide information on contact pressure to a user under the control of the processor 430. In this case, the guide information on contact pressure may include a position of an object to come into contact with the pulse wave measurer, reference contact pressure during measurement of a pulse wave signal, and/or contact pressure actually measured during measurement of a pulse wave signal, but is not limited thereto.

For example, upon receiving a request for measuring bio-information, the output interface 440 may visually display information on the reference contact pressure to be applied by a user during a measurement time period. Further, the output interface 440 may output actual contact pressure information which is actually measured by the contact pressure measurer 420 during measurement of a pulse wave signal. In addition, the output interface 440 may output information on a difference between the reference contact pressure and the actual contact pressure during the measurement time period.

The storage 450 may store various types of reference information, processing results of the pulse wave measurer 410, the contact pressure measurer 420, and/or the processor 430. In particular, various types of reference information may include user information including a user's age, gender, and/or health state, guide information on contact pressure, a linear function equation required for measuring bio-information, a standard equation for calculating a coefficient, and/or information for calibrating a linear function equation, but is not limited thereto.

In this case, the storage 450 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and an optical disk, but is not limited thereto.

The communication interface 460 may communicate with the external device 470 under the control of the processor 430 to cooperate with the external device 470 to perform various operations associated with measurement of bio-information. For example, the communication interface 460 may transmit a measurement result of pulse waves, a measurement result of contact pressure, and/or a processing result of the processor 430 to the external device 470, so that the external device 470 may manage a bio-information history for a user, may perform monitoring of a user's health state, may output the bio-information history and a monitoring result of the user's health state.

In another example, the communication interface 460 may receive, from the external device 470, information on a linear function equation required for measuring bio-information, reference information for calibration of the linear function equation. The received information may be stored in the storage 450.

In this case, the external device 470 may include a smartphone, a tablet PC, a desktop computer, and/or a laptop computer, and may also include devices of medical institutions, including a cuff-type blood pressure, but the external device 470 is not limited thereto.

Further, the communication interface 460 may communicate with the external device by using Bluetooth communication, Bluetooth Low Energy (BLE) communication, Near Field Communication (NFC), WLAN communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, 3G communication, 4G communication, and/or 5G communication. However, this is merely exemplary and is not intended to be limiting.

Figure 5A:
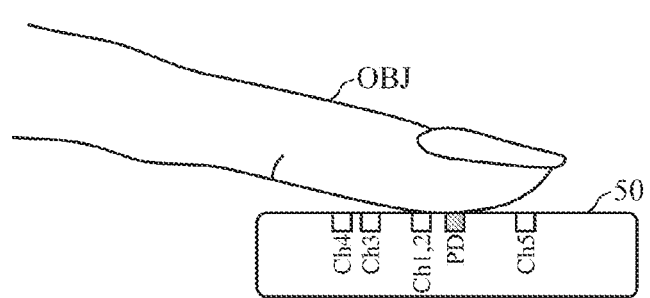
FIGS. 5A and 5B are diagrams illustrating a pulse wave sensor according to an exemplary embodiment.
Figure 5B:
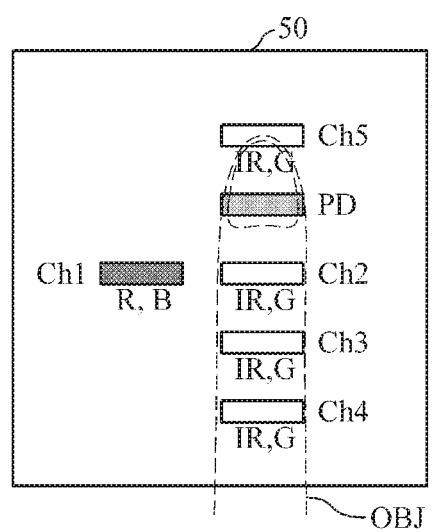

FIGS. 5A and 5B are diagrams illustrating a pulse wave sensor according to an exemplary embodiment. The pulse wave sensor 50 illustrated in FIGS. 5A and 5B are an example of the pulse wave measurers 110 and 410 of the bio-information measuring apparatuses 100 and 400. A shape of the pulse wave sensor 50 is not limited to a square shape illustrated therein, and may be various shapes such as a circular shape.

As illustrated in FIGS. 5A and 5B, the pulse wave sensor 50 may include a plurality of light emitters (e.g., a plurality of channels ch1, ch2, ch3, ch4, and ch5), so as to measure pulse wave signals in a wide region of a finger OBJ. The plurality of channels may be disposed at different distances from a light receiver PD. In this case, the light receiver PD may be two or more in number. Further, each of the channels ch1, ch2, ch3, ch4, and ch5 may include a plurality of light sources which emit light of one or more wavelengths, e.g., an infrared wavelength (IR), a green wavelength (G), and a blue wavelength (B); and the light sources of each of the channels ch1, ch2, ch3, ch4, and ch5 may emit light of different wavelengths as needed.

FIGS. 6A to 6F are diagrams illustrating measuring blood pressure by using a plurality of pulse wave signals according to an exemplary embodiment.

Figure 6A:
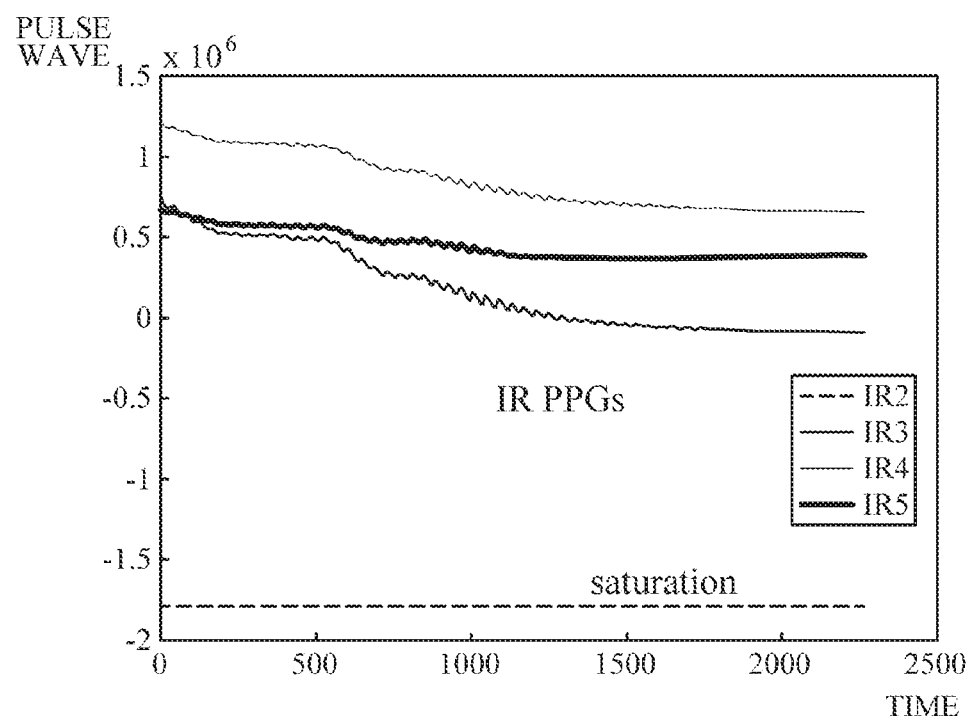
FIGS. 6A, 6B, 6C, 6D, 6E, and 6F illustrate measuring blood pressure by using a plurality of pulse wave signals according to an exemplary embodiment.
Figure 6B:
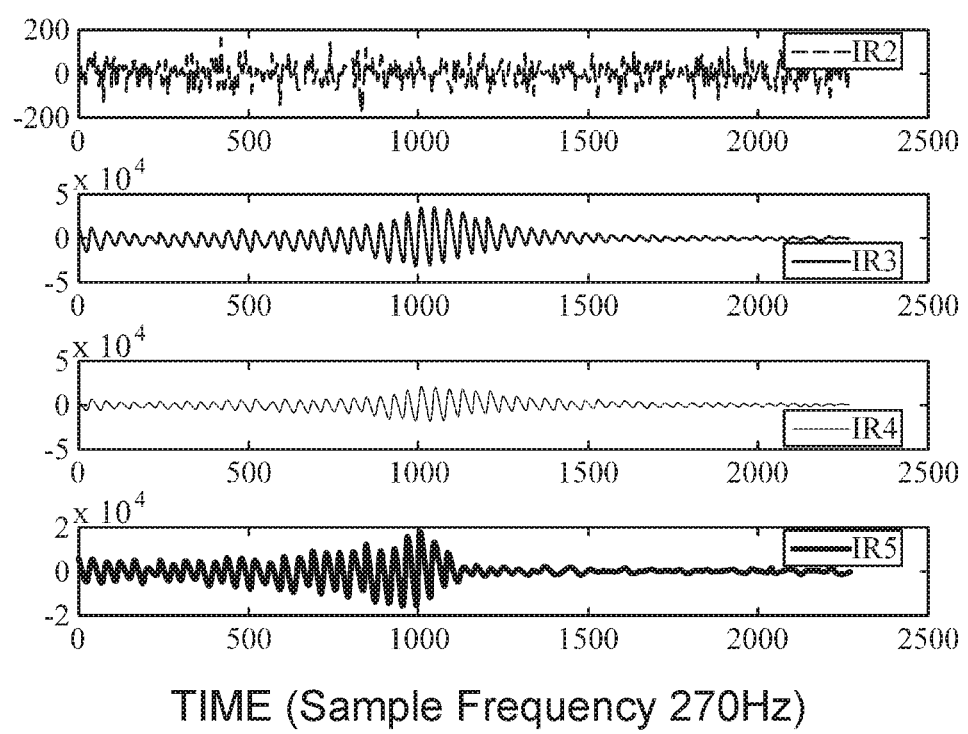

FIGS. 6A and 6B are diagrams illustrating pulse wave signals measured at the infrared wavelength (IR) by four channels ch2, ch3, ch4, and ch5 among the plurality of channels ch1, ch2, ch3, ch4, and ch5 of the pulse wave sensor 50 illustrated in FIG. 5A.

Figure 6C:
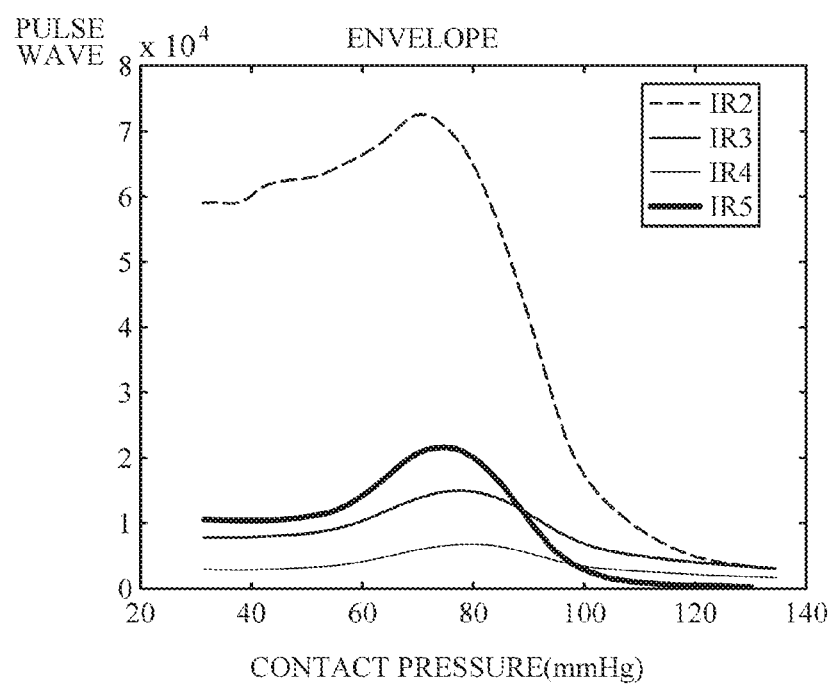
Figure 6D:
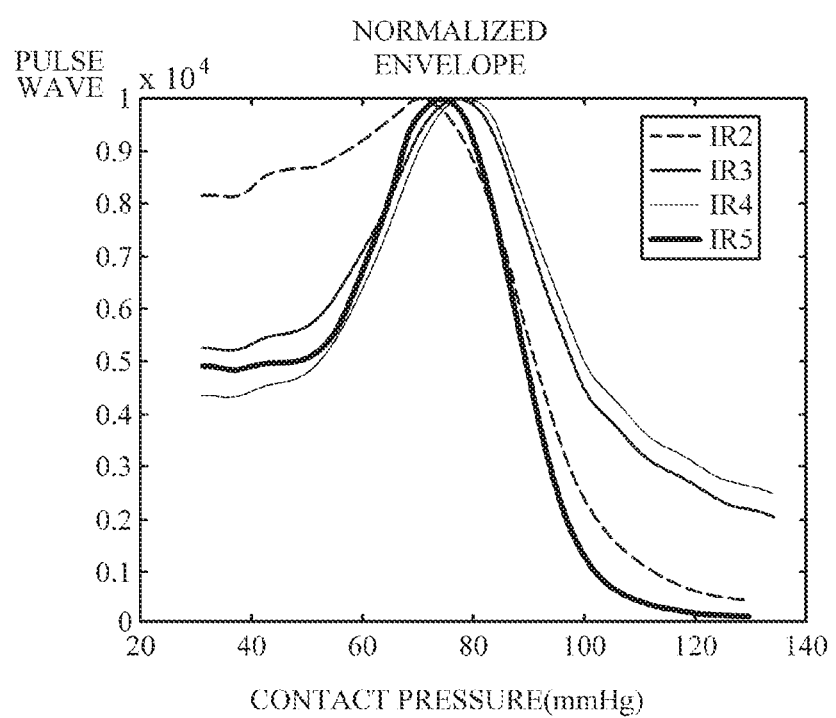

FIG. 6C is a graph showing oscillometric envelopes obtained based on contact pressure values for the pulse wave signals illustrated in FIGS. 6A and 6B. The pulse wave measurer 110/410 may measure the pulse wave signals from a user (e.g., a wrist or a finger of the user) while the user gradually increases or decreases the contact pressure between the user and the pulse wave measurer 110/410. The processor 130 may identify the oscillometric envelopes in a contact pressure domain as shown in FIG. 6, and may obtain bio-information based on a combination of the oscillometric envelopes. The oscillometric envelopes may represent changes of amplitudes of the pulse wave signals while the contact pressure gradually increases or decrease. As illustrated in FIG. 6C, maximum peak points of the envelopes are different for each wavelength/each channel. FIG. 6D is a diagram illustrating a maximum amplitude value normalized to 1, in the case where the maximum amplitude values at the maximum peak points of the envelopes are different.

Figure 6E:
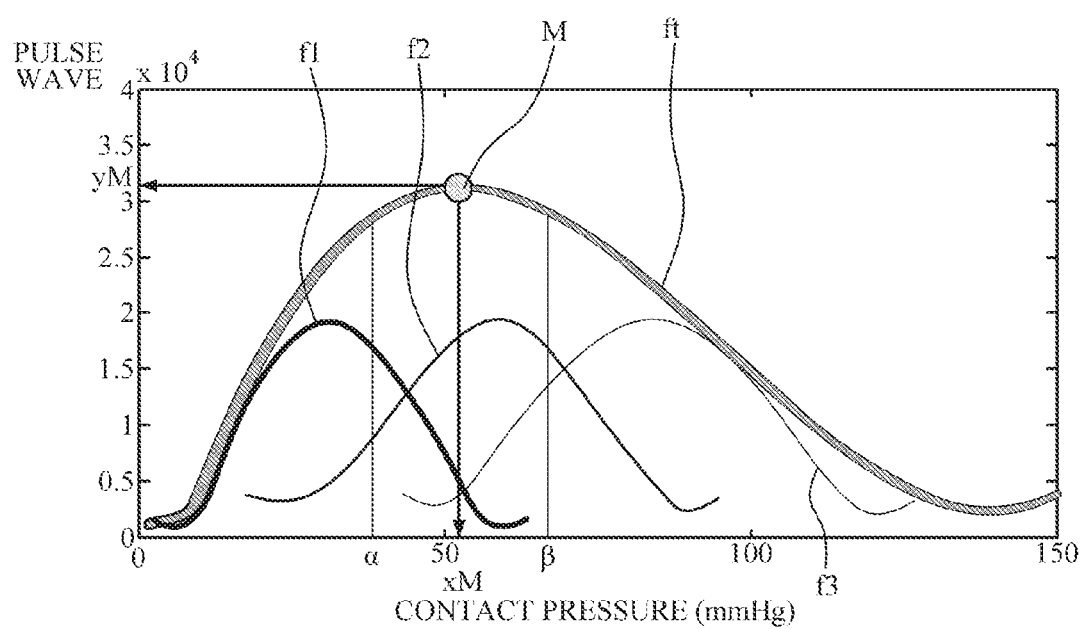

FIG. 6E is a diagram illustrating a combined envelope ft obtained by combining envelopes f1, f2, and f3 created for each channel. For example, the processors 130 and 430 of the bio-information measuring apparatuses 100 and 400 may measure blood pressure by using the combined envelope ft. Here, blood pressure is merely an example used for convenience of explanation, and is not intended to be limiting.

The processors 130 and 430 may detect a maximum peak point M from the combined envelope ft, and may extract features for measuring blood pressure. For example, as illustrated therein, the processors 130 and 430 may extract a contact pressure value xM or an amplitude value yM at the maximum peak point M as features.

Upon extracting features for measuring bio-information, the processors 130 and 430 may measure blood pressure based on the extracted features. For example, the processors 130 and 430 may determine the contact pressure value xM at the maximum peak point M to be the MAP, and may determine contact pressure values at certain points α and β, which are to the left and right of the MAP, to be the DBP and the SBP.

Figure 6F:
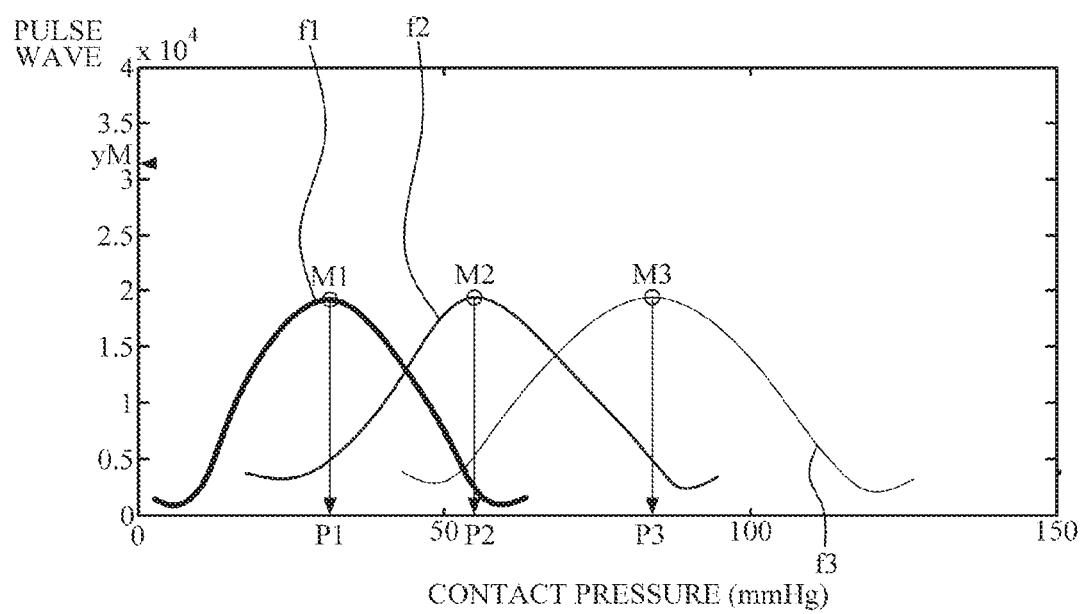

FIG. 6F is a diagram illustrating an example of measuring blood pressure by extracting features from each of the envelopes f1, f2, and f3 created for each channel. For example, the processors 130 and 430 may detect maximum peak points M1, M2, and M3 from each of the envelopes f1, f2, and f3, and may extract contact pressure values P1, P2, and P3 at the maximum peak points M1, M2, and M3 as features for measuring blood pressure. The processors 130 and 430 may calculate the MAP by applying the extracted contact pressure values P1, P2, and P3 in a linear function equation as described above. Further, the processors 130 and 430 may determine contact pressure values at certain points, which are to the left and right of the MAP, to be the DBP and the SBP.

Figure 7:
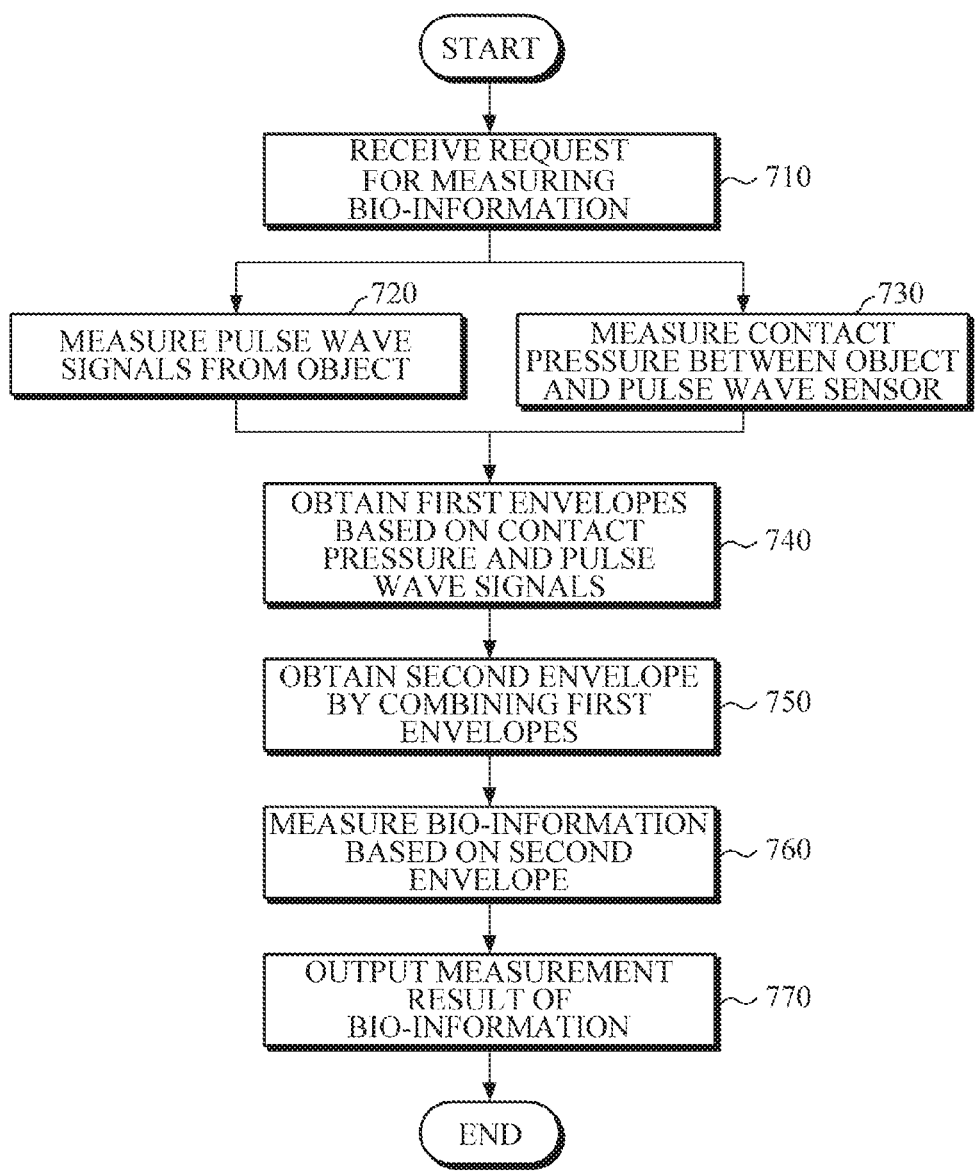
FIG. 7 is a flowchart illustrating a bio-information measuring method according to an exemplary embodiment.

FIG. 7 is a flowchart illustrating a bio-information measuring method according to an exemplary embodiment.

The bio-information measuring method of FIG. 7 may be an example of a bio-information measuring method performed by the bio-information measuring apparatus 100. The bio-information measuring method is described above in detail with reference to FIGS. 1 to 3, such that the description thereof will be briefly made below.

The bio-information measuring apparatus 100 may receive a request for measuring bio-information in operation 710. The request for measuring bio-information may be input by a user, or may be received from a connected external device. However, the request is not limited thereto, and it may be determined to receive the request automatically at predetermined intervals. Upon receiving the request for measuring bio-information, the bio-information measuring apparatus 100 may provide guide information for guiding contact pressure to a user. For example, the bio-information measuring apparatus 100 may display an image that prompts the user to gradually increase or decrease the contact pressure exerted onto the pulse wave measurer 110/410. In a case where the bio-information measuring apparatus 100 is wearable around a wrist, the bio-information measuring apparatus 100 may display an image that prompts the user to clench or relax his/her hand slowly, or prompts the user to clench and relax his/her hand repeatedly while the bio-information measuring apparatus 100 is measuring the bio-information of the user.

Then, the bio-information measuring apparatus 100 may measure a plurality of pulse wave signals from an object by using a pulse wave sensor 50 for a predetermined period of time in operation 720, and at the same time, may measure contact pressure between the pulse wave sensor 50 and the object in operation 730. Once contact pressure between the pulse wave sensor 50 and the object is changed during measurement of the pulse wave signals, the pulse wave signals are changed. In this case, the plurality of pulse wave signals may have wavelengths measured in a wide region of an object, and may have different wavelengths.

Subsequently, the bio-information measuring apparatus 100 may obtain first envelopes for each of the plurality of pulse wave signals by using the measured contact pressure in operation 740. For example, as described above, the bio-information measuring apparatus 100 may obtain a peak-to-peak amplitude value for each of the pulse wave signals, and may obtain oscillometric envelopes, which represent an oscillometric waveform of contact pressure versus pulse wave signal, by plotting contact pressure at the same measurement time as the peak-to-peak amplitude value, the envelope obtainer 210 may obtain. In particular, the peak-to-peak value may be extracted by subtracting a negative amplitude value from a positive amplitude value of a waveform at each measurement time in a pulse wave signal, e.g., a quadratic differential signal Next, upon obtaining the plurality of first envelopes, the bio-information measuring apparatus 100 may obtain a second envelope by combining the obtained plurality of first envelopes in operation 750. For example, the bio-information measuring apparatus 100 may obtain the combined one second envelope by applying the plurality of first envelopes in a pre-defined linear function equation.

Then, the bio-information measuring apparatus 100 may measure bio-information based on the obtained second envelope in operation 760. For example, the bio-information measuring apparatus 100 may extract features that are used for measuring bio-information from the obtained one second envelope, and may measure bio-information by using the extracted features.

Subsequently, upon measuring bio-information, the bio-information measuring apparatus 100 may output a measurement result of bio-information in operation 770. For example, the bio-information measuring apparatus 100 may control an output module to provide the measured bio-information, the measured plurality of pulse wave signals, and the measured contact pressure values to a user. In this case, examples of the output module may include a display module, a speaker, and/or a haptic device.

Figure 8:
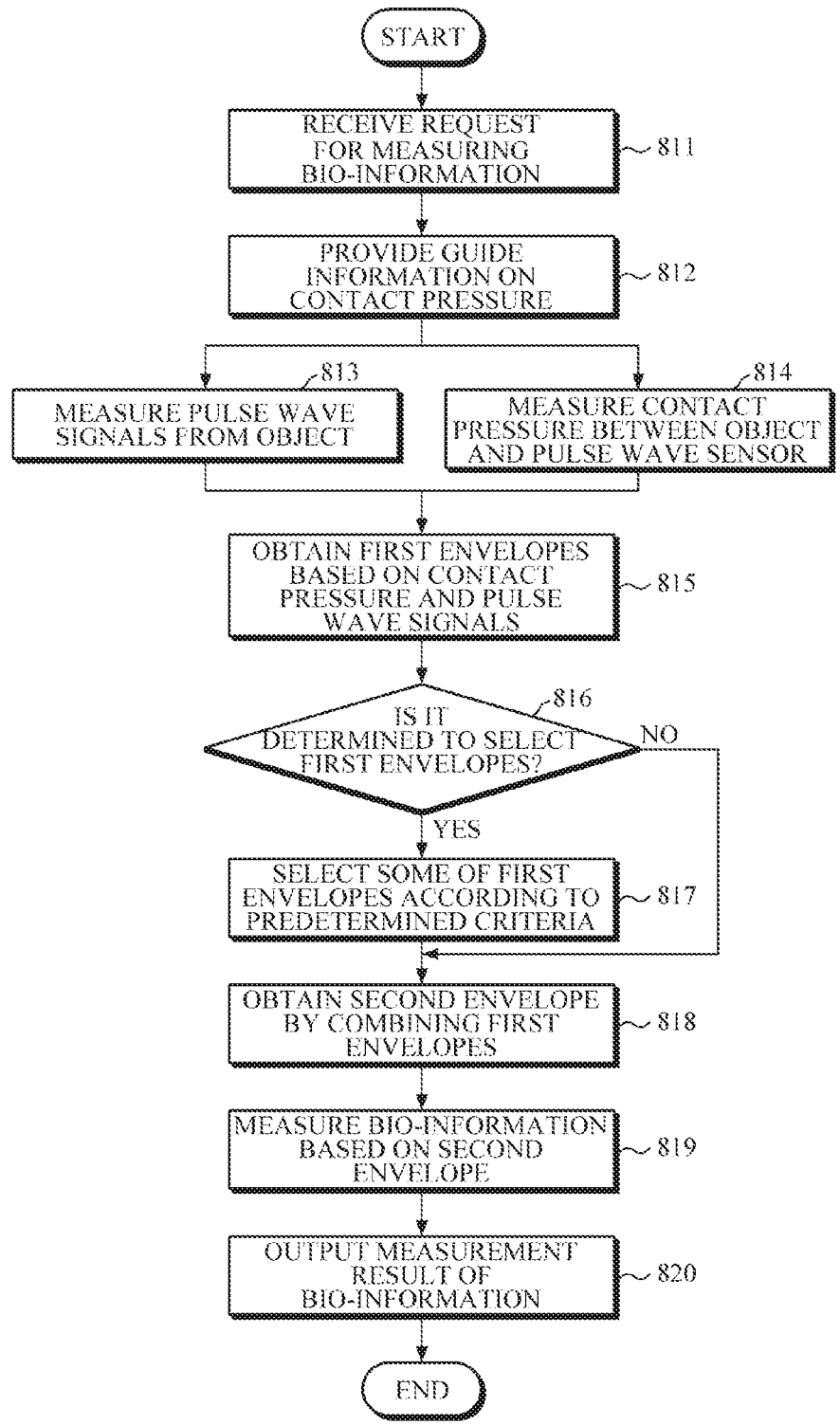
FIG. 8 is a flowchart illustrating a bio-information measuring method according to another exemplary embodiment.

FIG. 8 is a flowchart illustrating a bio-information measuring method according to another exemplary embodiment.

The bio-information measuring method of FIG. 8 may be another example of a bio-information measuring method performed by the bio-information measuring apparatus 100 of FIG. 1.

Referring to FIG. 8, the bio-information measuring apparatus 100 may receive a request for measuring bio-information in operation 811. The request for measuring bio-information may be input by a user, from an external device.

Then, the bio-information measuring apparatus 100 may provide a user with guide information for guiding contact pressure in operation 812. For example, the guide information for guiding contact pressure may be a reference contact pressure value to be increased or decreased by a user for an object or a pulse wave sensor while the pulse wave sensor measures pulse wave signals from an object. Alternatively, the guide information for guiding contact pressure may include action information of a user for guiding the user to change contact pressure during a measurement time. Further, the guide information may include various types of information for guiding proper contact pressure while the pulse wave sensor measures pulse wave signals, and the guide information may be provided using various visual or non-visual methods.

Subsequently, the bio-information measuring apparatus 100 may measure a plurality of pulse wave signals from an object by using the pulse wave sensor in operation 813, and at the same time, may measure contact pressure between the object and the pulse wave sensor in operation 814. The pulse wave signals may be multi-wavelength pulse wave signals.

The guiding of contact pressure in operation 812 may continue during the measurement of pulse wave signals in operation 813 and the measurement of contact pressure in operation 814.

Next, the bio-information measuring apparatus 100 may obtain a plurality of first envelopes in operation 815 based on the plurality of pulse wave signals obtained in operation 813 and the contact pressure signal obtained in operation 814.

Then, the bio-information measuring apparatus 100 may determine whether to select some of the first envelopes for use in measuring bio-information from among the obtained first envelopes in operation 816. In particular, information on whether to select some of the first envelopes may be preset in the bio-information measuring apparatus 100.

Subsequently, upon determining to select some of the first envelopes in operation 816, the bio-information measuring apparatus 100 may select at least some of the first envelopes from among the plurality of first envelopes according to predetermined criteria in operation 817. In this case, the predetermined criteria may include an examination position, the measured contact pressure values, amplitude values at peak points of the plurality of first envelopes, a distance between a light source and a light receiver for each of the plurality of first envelopes, and/or information on whether a maximum peak amplitude value is within a predetermined range of contact pressure values but the criteria are not limited thereto.

Next, upon determining not to select some of the first envelopes in operation 816, the bio-information measuring apparatus may obtain a second envelope in operation 818 by combining all the first envelopes obtained in operation 815 or by combining the first envelopes selected in operation 817. For example, the bio-information measuring apparatus 100 may obtain the one second envelope by substituting the plurality of first envelopes in a linear function equation.

Then, the bio-information measuring apparatus 100 may measure bio-information based on the obtained second envelope in operation 819, and may output a measurement result of bio-information in operation 820.

Figure 9:
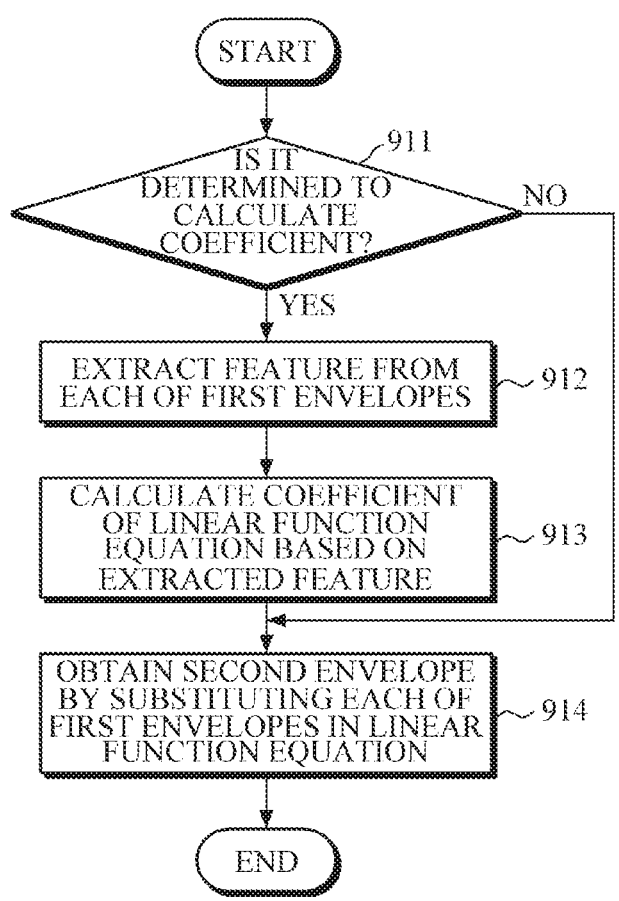
FIG. 9 is a flowchart illustrating obtaining a second envelope of FIGS. 7 and 8 according to an exemplary embodiment.

FIG. 9 is a flowchart illustrating obtaining the second envelope of FIGS. 7 and 8 according to an exemplary embodiment.

Referring to FIG. 9, the obtaining of the second envelope in operations 750 and 818 of FIGS. 7 and 8 may include determining whether to calculate a coefficient of a linear function equation for combining the plurality of first envelopes in operation 911. In this case, information on whether to calculate the coefficient of the linear function equation may be preset.

Then, upon determining to calculate the coefficient in operation 911, the bio-information measuring apparatus 100 may extract features from each of the plurality of first envelopes in operation 912. For example, the features extracted from each of the plurality of first envelopes may include a maximum amplitude value at a maximum peak point.

Subsequently, based on the extracted features, the bio-information measuring apparatus 100 may calculate the coefficient of the linear function equation to be applied in operation 913. For example, based on each maximum amplitude value extracted from each of the first envelopes, the bio-information measuring apparatus 100 may calculate the coefficient for each of the first envelopes.

Next, the bio-information measuring apparatus 100 may obtain a second envelope in operation 914 by applying each of the first envelopes in a linear function equation, to which the coefficient calculated in operation 913 is applied, or a pre-defined coefficient is applied in response to determination not to calculate a coefficient in operation 911.

Figure 10:
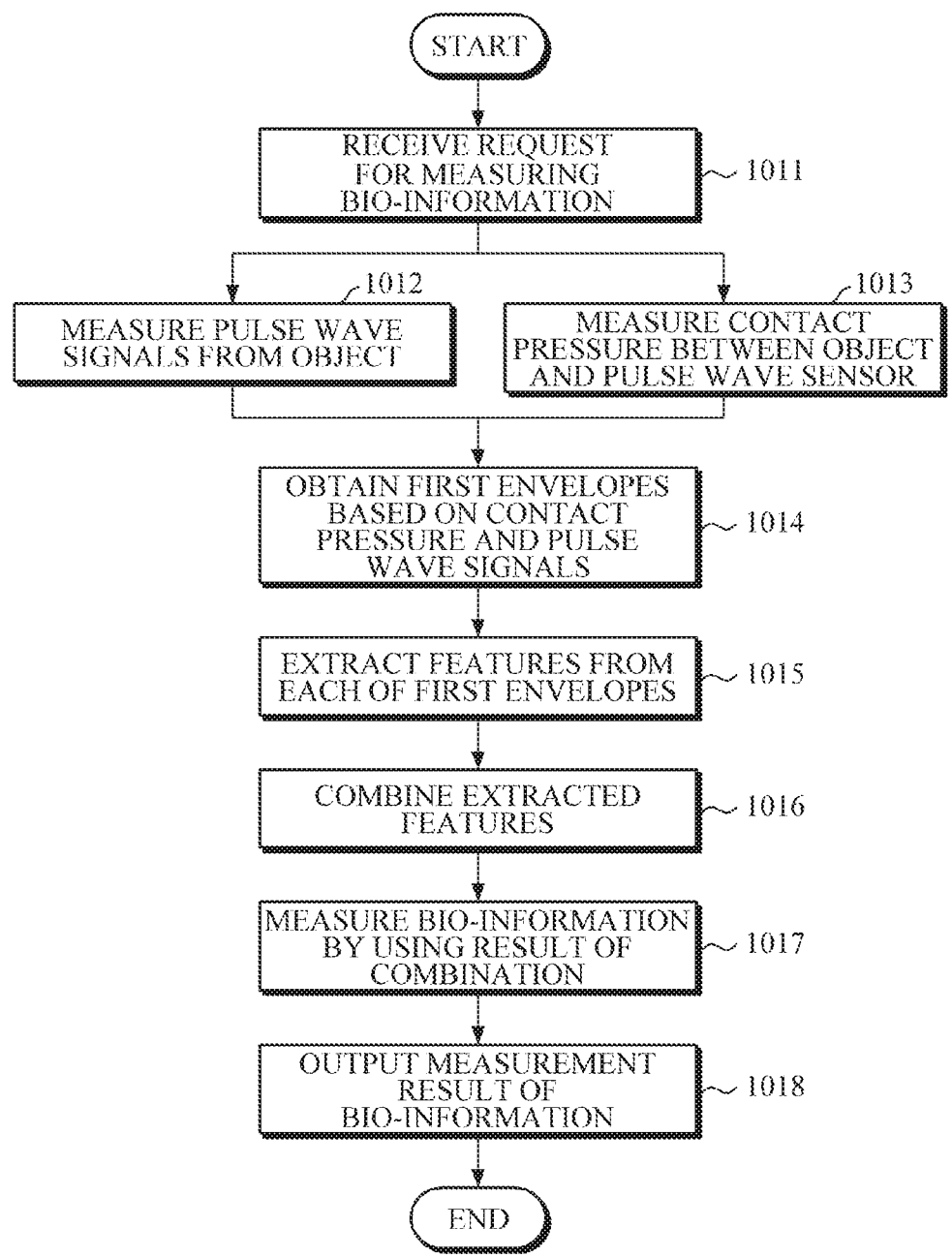
FIG. 10 is a flowchart illustrating a bio-information measuring method according to another exemplary embodiment.

FIG. 10 is a flowchart illustrating a bio-information measuring method according to another exemplary embodiment.

The bio-information measuring method of FIG. 10 may be yet another example of a bio-information measuring method performed by the bio-information measuring apparatus of FIG. 1, which will be described briefly below in order to avoid duplicated description.

Referring to FIG. 10, upon receiving a request for measuring bio-information in operation 1011, the bio-information measuring apparatus 100 may measure a plurality of pulse wave signals from an object in operation 1012, and at the same time, may measure contact pressure between the object and the pulse wave sensor in operation 1013.

Then, the bio-information measuring apparatus 100 may obtain a plurality of first envelopes based on the contact pressure and the plurality of pulse wave signals in operation 1014.

Subsequently, the bio-information measuring apparatus 100 may extract features from each of the obtained first envelopes in operation 1015. For example, the features may include contact pressure values at a maximum peak point of each of the first envelopes, but are not limited thereto as described above.

Next, the bio-information measuring apparatus 100 may obtain the combined one feature by combining the extracted features in operation 1016. In this case, by using the linear function equation as represented by the aforementioned Equation 4, the bio-information measuring apparatus 100 may combine the features into one feature. In this case, the bio-information measuring apparatus 100 may select some of the features from among the obtained features according to predetermined criteria, and may combine the selected features into one.

Then, the bio-information measuring apparatus 100 may measure bio-information by using a result of the combination in operation 1017, and may output a measurement result of bio-information to a user in operation 1018. For example, the bio-information measuring apparatus 100 may determine the combined one feature to be MAP, and based on the MAP, the bio-information measuring apparatus 100 may measure the SBP and the DBP.

Figure 11:
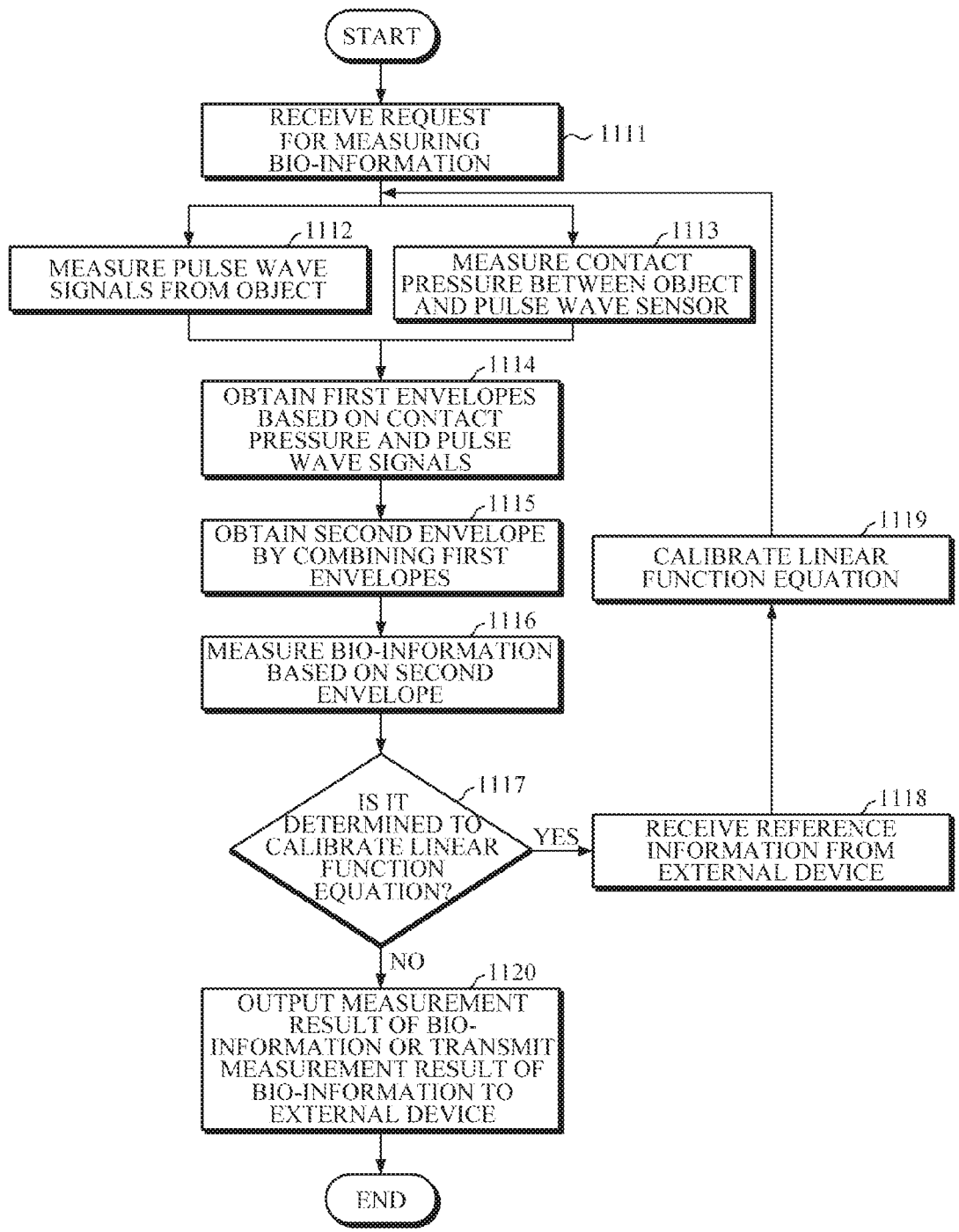
FIG. 11 is a flowchart illustrating a bio-information measuring method according to another exemplary embodiment.

FIG. 11 is a flowchart illustrating a bio-information measuring method according to another exemplary embodiment.

The bio-information measuring method of FIG. 4 may be an example of a bio-information measuring method performed by the bio-information measuring apparatus 400 of FIG. 4.

Referring to FIG. 11, upon receiving a request for measuring bio-information in operation 1111, the bio-information measuring apparatus 400 may measure a plurality of pulse wave signals from an object in operation 1112, and at the same time, may measure contact pressure between the object and the pulse wave sensor by using a contact pressure sensor in operation 1113.

Then, the bio-information measuring apparatus 100 may obtain a plurality of first envelopes based on the contact pressure and the plurality of pulse wave signals in operation 1114.

Subsequently, the bio-information measuring apparatus 100 may obtain one second envelope by combining the obtained first envelopes in operation 1115. In this case, the bio-information measuring apparatus 100 may obtain the one second envelope by applying the plurality of first envelopes in a pre-defined linear function equation.

Next, the bio-information measuring apparatus 100 may measure bio-information by using the one obtained second envelope in operation 1116.

Then, the bio-information measuring apparatus 100 may determine whether to calibrate a linear function equation based on the measurement result of bio-information in operation 1117. For example, based on a measurement history of bio-information, the bio-information measuring apparatus 100 may determine that there is abnormality in the measurement result of bio-information. However, determination on the calibration is not limited thereto, and the determination whether to calibrate in operation 1117 is not necessarily performed after the measurement of bio-information in operation 1116 but may be performed in any order.

Subsequently, upon determining to calibrate a linear function equation or a coefficient of the linear function equation in operation 1117, the bio-information measuring apparatus 100 may be connected to an external device through communication to receive reference information required for calibrating the linear function equation in operation 1118. In this case, the reference information may be a linear function equation obtained by an external device, information on a coefficient, or information on cuff pressure measured by a cuff-type blood pressure measuring apparatus. However, the information is not limited thereto.

Then, the bio-information measuring apparatus 100 may calibrate the linear function equation based on the received reference information in operation 1119, and may perform again operations subsequent to the measurement of a plurality of pulse wave signals in operation 1112 and the measurement of contact pressure in operation 1113.

Subsequently, upon determining that calibration is not required in operation 1117, the bio-information measuring apparatus 100 may output a measurement result of bio-information to a user in operation 1120.

Figure 12:
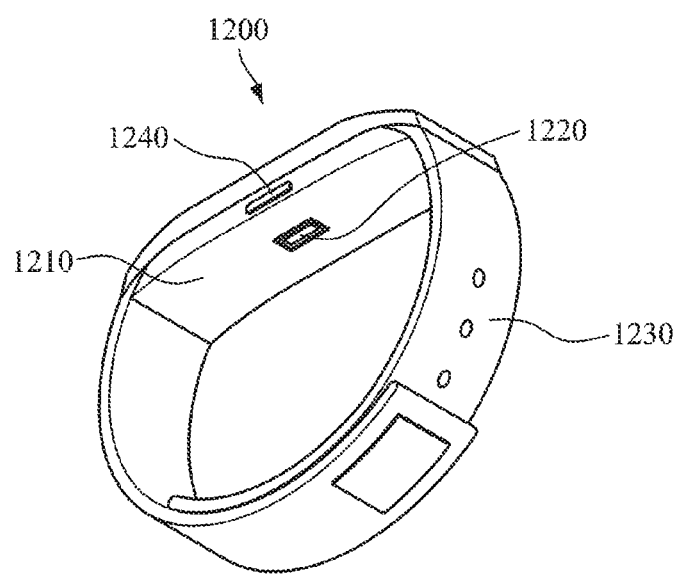
FIG. 12 is a diagram illustrating a wearable device, to which a bio-information measuring apparatus is applied according to an exemplary embodiment.

FIG. 12 is a diagram illustrating a wearable device, to which a bio-information measuring apparatus is applied according to an exemplary embodiment. Various embodiments of the above-described bio-information measuring apparatus may be mounted in a smart watch or a smart band-type wearable device which is wearable on a wrist as illustrated herein. However, the wearable device is merely an example used for convenience of explanation, and it should not be construed that application of the embodiments is limited to a smart watch or a smart band-type wearable device.

Referring to FIG. 12, the wearable device 1200 includes a main body 1210 and a strap 1230.

The strap 1230 may be flexible, and may be connected to both ends of the main body 1210 to be bent around a user's wrist or may be bent in a manner which allows the strap 1230 to be detached from a user's wrist. Alternatively, the strap 1230 may be formed as a band that is not detachable. In this case, air may be injected into the strap 1230 or an airbag may be included in the strap 1230, so that the strap 1230 may have elasticity according to a change in pressure applied to the wrist, and the change in pressure of the wrist may be transmitted to the main body 1210.

A battery, which supplies power to the wearable device 1200, may be embedded in the main 1210 or the strap 1230.

Further, the wearable device 1200 includes a sensor part 1220 for measuring a pulse wave signal and a contact pressure signal from an object, and a processor for measuring bio-information of a user by using the pulse wave signal and the contact pressure signal which are measured by the sensor part 1220.

The sensor part 1220 includes a pulse wave sensor which is mounted at a bottom portion of the main body 1210 to be exposed to a portion that comes into contact with an object (e.g., a user's wrist) and measures a pulse wave signal from the object, and a contact pressure sensor which is mounted in the main body 1210 and measures a contact pressure signal between the pulse wave sensor and the object.

The pulse wave sensor includes a multi-channel light emitter including one or more light sources for emitting light onto an object, and a light receiver including one or more detectors for detecting light emanating from the object. The pulse wave sensor may measure a plurality of pulse wave signals, having different wavelengths, from the object.

The contact pressure sensor may measure contact pressure of an object, which is transmitted to the main body 1210 through the strap 1230 which is wrapped around the wrist to secure the main body 1210 to the object.

The processor may control the sensor part 1220 by generating a control signal according to a request for measuring bio-information of a user, and may measure bio-information, such as blood pressure, by using the pulse wave signal and/or the contact pressure signal that are measured by the sensor part 1220, which is described above in detail such that description thereof will be omitted.

Upon receiving a request for measuring bio-information from a user, the processor may guide contact pressure through a display which is not shown, so that a user may apply pressure to the main body 1210 to change contact pressure between the pulse wave sensor and the object.

The display may be mounted on a front surface of the main body 1210, and may visually output guide information on contact pressure and/or a measurement result of bio-information.

A user may change a thickness of the wrist, on which the main body 1210 is worn, by making hand movements (e.g., closing or opening their fist or spreading out their fingers one by one) according to guide information on contact pressure displayed on the display. In this case, a change in the thickness of the wrist leads to a change in tension of the strap wrapped around the wrist, thereby causing a change in contact pressure between a top portion of the wrist and the pulse wave sensor. Alternatively, by applying pressure while touching a front surface of the main body 1210 with a finger of a hand, on which the main body 1210 is not worn, according to guide information on contact pressure, a user may change contact pressure between the top portion of the wrist and the pulse wave sensor.

The processor may manage, in a storage device, various types of information such as a measurement result of bio-information (e.g., measured blood pressure values), blood pressure history information, and pulse wave signals and contact pressure signals used for measuring each blood pressure value, extracted features. In addition, the processor may generate additional information required for managing health of a user, such as alarm or warning information associated with the measured bio-information, and development of change in health state, and may manage the generated information in the storage device.

Further, the wearable device 120 may include a manipulator 1240 which receives a control command of a user and transmits the received control command to the processor. The manipulator 1240 may be mounted on a side surface of the main body 1210, and may include a function for inputting a command to turn on/off the wearable device 1200.

Moreover, the wearable device 1200 may include a communication interface for transmitting and receiving various data with an external device, and various other modules for performing additional functions provided by the wearable device 1200.

Figure 13A:
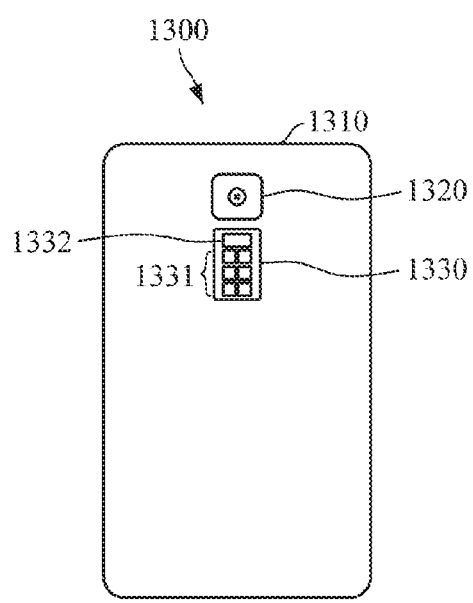
FIGS. 13A and 13B are diagrams illustrating a smart device, to which a bio-information measuring apparatus is applied, according to an exemplary embodiment.
Figure 13B:
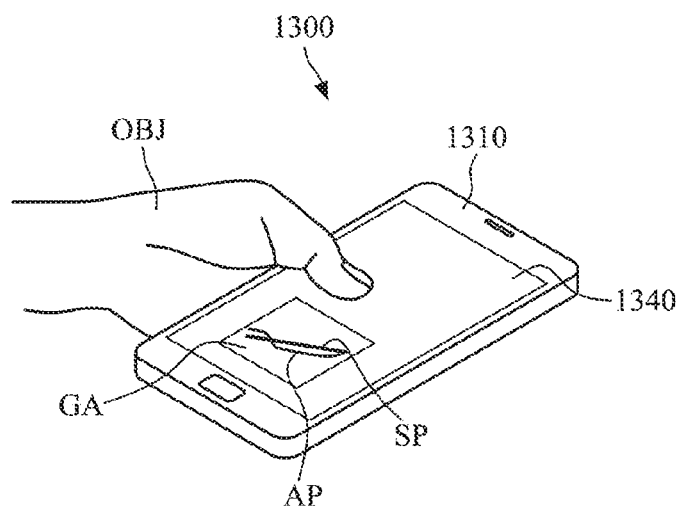

FIGS. 13A and 13B are diagrams illustrating a smart device, to which a bio-information measuring apparatus is applied according to an exemplary embodiment. The various embodiments of the above-described bio-information measuring apparatus may be applied to a smart device such as a smartphone, or a tablet PC.

Referring to FIGS. 13A and 13B, the smart device 1300 includes a pulse wave sensor 1330 mounted on a rear surface of a main body 1310 to be exposed to the outside. In this case, the pulse wave sensor 1330 may include a multi-channel light emitter 1331 and a light receiver 1332. Each channel of the light emitter 1331 includes one or more light sources, each of which may be a light emitting diode (LED), and at least some of the light sources may emit light of different wavelengths. The light receiver 1332 may be a photo diode, or a photo transistor.

Further, a contact pressure sensor for measuring contact pressure between the pulse wave sensor and an object (OBJ) (e.g., a finger) may be embedded in the main body 1310.

A display 1340 may be mounted on a front surface of the main body 1310. The display 1340 may have an area (GA) for displaying guide information on contact pressure at a predetermined position under the control of the processor embedded in the main body as illustrated in FIGS. 13A and 13B. In addition, the display 1340 may visually display, in the area (GA), information on a change (SP) in reference contact pressure to be increased or decreased by a user for the pulse wave sensor 1330 while the pulse wave sensor 1330 measures pulse wave signals from a user's finger, and/or information on a change (AP) in actual contact pressure measured by a contact pressure sensor while the pulse wave sensor 1330 measures pulse wave signals.

Moreover, an image sensor 1320 may be mounted in the main body 1310. When a user's finger approaches the pulse wave sensor 1330 to measure a pulse wave signal, the image sensor 1320 may capture an image of the finger and may transmit the captured image to the processor. In this case, based on the image of the finger, the processor may identify a relative position of the finger with respect to an actual position of the pulse wave sensor, and may provide the relative position of the finger to the user through the display 1340.

Various other modules for performing many functions of the aforementioned bio-information measuring apparatus may be mounted in the smart device 1300, and detailed description thereof will be omitted.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A bio-information measuring apparatus comprising:
a pulse wave measurer comprising a plurality of different light emitters and a light receiver to measure a plurality of pulse wave signals by detecting light that is emitted from the plurality of different light emitters and then is reflected from an object;
a pressure sensor configured to measure a contact pressure between the object and the pulse wave measurer; and
a processor configured
to obtain a plurality of first envelopes,
wherein each of the plurality of first envelopes represents an amplitude of each of the plurality of pulse wave signals in a domain of the contact pressure,
to obtain a second envelope by adding the plurality of first envelopes,
to measure bio-information based on the second envelope,
to determine an abnormality of the measured bio-information by comparing the measured bio-information to a normal range of the bio-information of the object, and
to generate a warning or an advisory to the object according to the determined abnormality.

2. The bio-information measuring apparatus of claim 1, wherein the plurality of different light emitters are disposed at different distances from the light receiver.

3. The bio-information measuring apparatus of claim 1, wherein the light that is emitter from the plurality of different light emitters is of different wavelengths.

4. The bio-information measuring apparatus of claim 1, wherein the processor comprises an envelope combiner configured to obtain the second envelope by applying the plurality of first envelopes in a linear function equation.

5. The bio-information measuring apparatus of claim 4, wherein the envelope combiner is further configured to obtain the second envelope by selecting at least two first envelopes from among the plurality of first envelopes according to predetermined criteria, and by applying the selected at least two first envelopes in the linear function equation.

6. The bio-information measuring apparatus of claim 4, wherein the envelope combiner is further configured to obtain a coefficient of the linear function equation for each of the plurality of first envelopes.

7. The bio-information measuring apparatus of claim 6, wherein the envelope combiner is further configured to obtain a reciprocal number of a maximum amplitude value of each of the plurality of first envelopes as the coefficient for each of the plurality of first envelopes.

8. The bio-information measuring apparatus of claim 4, wherein the processor comprises a calibrator configured to, based on at least one of a measurement history of the bio-information, a health state of a user, a position of the object, a state of the object, and an intensity of a light emitted from the pulse wave measurer, determine whether to perform calibration on the linear function equation.

9. The bio-information measuring apparatus of claim 1, wherein the processor further comprises:
a feature extractor configured to extract features from the second envelope; and
a measurer configured to obtain the bio-information based on the extracted features, and
wherein the features comprise at least one of a contact pressure value and an amplitude value at a maximum peak point of the second envelope, and a contact pressure value and an amplitude value at multiple points in a predetermined range based on the maximum peak point.

10. The bio-information measuring apparatus of claim 1, wherein the bio-information comprises at least one of blood pressure, vascular age, degree of arteriosclerosis, aortic pressure waveform, vascular compliance, stress index, and degree of fatigue.

11. The bio-information measuring apparatus of claim 1, further comprising an output interface configured to output, upon receiving a request for measuring the bio-information, guide information comprising at least one of a position of the object that is in contact with the pulse wave measurer, a reference contact pressure value obtained during measurement of a reference pulse wave signal, and a contact pressure value measured during measurement of the plurality of pulse wave signals of the object.

12. A bio-information measuring method comprising:
measuring a plurality of pulse wave signals from an object by a pulse wave measurer;
measuring a contact pressure between the object and the pulse wave measurer;
obtaining a plurality of first envelopes, wherein each of the plurality of first envelops represents an amplitude of each of the plurality of pulse wave signals in a domain of the contact pressure;
obtaining a second envelope by adding the plurality of first envelopes; measuring bio-information based on the second envelope;
determining an abnormality of the measured bio-information by comparing the measured bio-information to a normal range of the bio-information of the object; and
generating a warning or an advisory to the object according to the determined abnormality.

13. The bio-information measuring method of claim 12, wherein the plurality of pulse wave signals are multi-wavelength pulse wave signals measured at a plurality of positions on the object.

14. The bio-information measuring method of claim 12, wherein the obtaining the second envelope comprises obtaining the second envelope by applying the plurality of first envelopes in a linear function equation.

15. The bio-information measuring method of claim 14, wherein the obtaining the second envelope comprises obtaining the second envelope by:
selecting at least two first envelopes from among the plurality of first envelopes according to predetermined criteria; and
applying the selected at least two first envelopes in the linear function equation.

16. The bio-information measuring method of claim 14, wherein the obtaining the second envelope comprises obtaining a coefficient of the linear function equation for each of the plurality of first envelopes.

17. The bio-information measuring method of claim 12, further comprising, upon receiving a request for measuring the bio-information, outputting guide information that prompts a user to gradually increase the contact pressure between the object and the pulse wave measurer.

18. The bio-information measuring method of claim 17, wherein the measuring the plurality of pulse wave signals comprises measuring the plurality of pulse wave signals while the guide information is displayed and the contact pressure between the object and the pulse wave measurer gradually increases.

19. A bio-information measuring apparatus comprising:
a pulse wave measurer comprising a plurality of different light emitters and a light receiver—to measure a plurality of pulse wave signals by detecting light that is emitted from the plurality of different light emitters and then is reflected from an object;
a pressure sensor configured to measure a contact pressure between the object and the pulse wave measurer; and
a processor configured
to obtain a plurality of envelopes,
wherein each of the plurality of envelopes represents an amplitude of each of the plurality of pulse wave signals in a domain of the contact pressure,
to obtain a second feature by adding a plurality of first features extracted from the plurality of envelopes,
to measure bio-information based on the second feature,
to determine an abnormality of the measured bio-information by comparing the measured bio-information to a normal range of the bio-information of the object, and
to generate a warning or an advisory to the object according to the determined abnormality.

20. The bio-information measuring apparatus of claim 19, wherein the plurality of different light emitters are disposed at different distances from the light receiver, and configured to emit light of different wavelengths.

21. The bio-information measuring apparatus of claim 19, wherein the processor comprises:
a feature extractor configured to extract from each of the plurality of envelopes, the plurality of first features, comprising a contact pressure value at a maximum peak point of each of the plurality of envelopes; and
a feature combiner configured to obtain the second feature, comprising a mean arterial pressure (MAP), by applying the plurality of first features in a linear function equation.

22. The bio-information measuring apparatus of claim 21, wherein the processor further comprises a measurer configured to measure a diastolic blood pressure (DBP) and a systolic blood pressure (SBP) based on the MAP.

23. A bio-information measuring apparatus comprising: a pressure sensor configured to measure a contact pressure between a user and a pulse wave measurer;
the pulse wave measurer comprising a plurality of different light emitters and a light receiver to measure a plurality of pulse wave signals by detecting light that is emitted from the plurality of different light emitters and then is reflected from the user,
wherein the plurality of pulse wave signals are measured while the contact pressure is gradually increasing or decreasing; and
a processor configured
to identify a plurality of envelopes,
wherein each of the plurality of envelopes is identified in each of the plurality of pulse wave signals in a contact pressure domain,
to obtain bio-information by adding the plurality of envelopes,
wherein each of the plurality of envelopes represents a change of an amplitude of each of the plurality of pulse wave signals while the contact pressure gradually increases or decreases,
to determine an abnormality of the obtained bio-information by comparing the obtained bio-information to a normal range of the bio-information of the user, and
to generate a warning or an advisory to the user according to the determined abnormality.

24. The bio-information measuring apparatus of claim 23, the processor is further configured to apply a plurality of weights to the plurality of envelopes, respectively, to obtain a weighted plurality of envelopes, and add up the weighted plurality of envelopes to obtain a sum of the plurality of envelopes.

* * * * *